(12) United States Patent
Ludin et al.

(10) Patent No.: US 7,671,009 B2
(45) Date of Patent: Mar. 2, 2010

(54) DERMOPHARMACEUTICALLY AND COSMETICALLY ACTIVE OLIGOPEPTIDES

(75) Inventors: Christian Ludin, Aesch (CH); Marc Heidl, Grenzach-Wyhlen (DE); Hugo Ziegler, Witterswil (CH)

(73) Assignee: DSM IP Assets B.V., Heerlen (NL)

( * ) Notice: Subject to any disclaimer, the term of this patent is extended or adjusted under 35 U.S.C. 154(b) by 807 days.

(21) Appl. No.: 10/493,856

(22) PCT Filed: Oct. 30, 2002

(86) PCT No.: PCT/CH02/00587

§ 371 (c)(1),
(2), (4) Date: Oct. 18, 2004

(87) PCT Pub. No.: WO03/037933

PCT Pub. Date: May 8, 2003

(65) Prior Publication Data

US 2005/0065090 A1 Mar. 24, 2005

(30) Foreign Application Priority Data

Oct. 30, 2001 (CH) ..................... 1986/01

(51) Int. Cl.
*A61K 38/00* (2006.01)
(52) U.S. Cl. ......................................................... 514/2
(58) Field of Classification Search .................. None
See application file for complete search history.

(56) References Cited

FOREIGN PATENT DOCUMENTS

| WO | WO 86/04334 | | 7/1986 |
|----|-------------|---|--------|
| WO | WO 00/15188 | | 3/2000 |
| WO | WO 00/62740 | * | 10/2000 |
| WO | WO 00/62743 | | 10/2000 |

OTHER PUBLICATIONS

MSDS sheet for TFA.*
Katayama K J "A pentapeptide from type I procollagen promotes extracellular matrix production," Biol Chem. May 15, 1993;268(14):9941-4.*

Katayama et al., A Pentapeptide from Type I Procollagen Promotes Extracellular Matrix Production; Journal of Biological Chemistry, 286, No. 14, pp. 9941-9944; May 15, 1993, Baltimore, MD, US.

* cited by examiner

*Primary Examiner*—Cecilia Tsang
*Assistant Examiner*—Thomas S Heard
(74) *Attorney, Agent, or Firm*—Hoffmann & Baron, LLP

(57) ABSTRACT

Oligopeptides and derivatives thereof, peptide analogs and derivatives thereof as well as pharmaceutically acceptable salts of these compounds, which correspond to general formula (I)

(I)

[chemical structure]

wherein
$R^1$ represents H, $-C(O)-R^7$, $-SO_2-R^7$, $-C(O)-OR^7$ or $-C(O)-N(R^7)_2$
$R^2$ represents, independent of one another, H or $-(C_1-C_4)$-alkyl,
$R^3$ and $R^6$ represent, independent of one another, $-(CH_2)_q-N(R^1)R^8$
$R^4$ and $R^5$ represent, independent of one another, $-CH_2-OR^2$, $-CH(CH_3)OR^8$ or $-CH_2-CH_2-OR^8$
$R^7$ represents hydrogen, optionally substituted $(C_1-C_{19})$-alkyl; optionally substituted $(C_1-C_{19})$-alkenyl; phenyl-$(C_1-C_4)$-alkyl whose phenyl radical is optionally substituted with amino in the para position
$R^8$ represents H, $-(C_1-C_4)$-alkyl, $-C(O)-R^7$, $-C(O)-OR^7$, $-C(O)-N(R^7)_2$ or $-SO_2-R^7$
X represents oxygen ($-O-$) or $-NH-$; or
$XR^7$, with X=O, also represents the esters of α-tocopherol, tocotrienol or retinol or the carboxylic acid (with $R^7$=H)
m, n, p represent, independent of one another, zero or 1 and q in $R^3$ and $R^6$ represent, independent of one another, an integer from 1 to 4, with the provision that the following conditions do not simultaneously occur: $R^4=-CH(CH_3)-OH$ and $R^5=-CH(CH_3)-OH$ and $R^6=-(CH_2)_4-NH_2$; dermopharmaceutically and/or cosmetically active compositions containing at least one compound of formula (I).

21 Claims, No Drawings

SEQUENCE LISTING

```
<160> NUMBER OF SEQ ID NOS: 39

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence:Subfragment

<400> SEQUENCE: 1

Lys Thr Thr Lys Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence:
      Palmitoylated pentapeptide
<220> FEATURE:
<221> NAME/KEY: LIPID
<222> LOCATION: (1)..(1)
```

```
<223> OTHER INFORMATION: PALMITATE (N-2 linked)

<400> SEQUENCE: 2

Lys Thr Thr Lys Ser
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence:Oligopeptide
<220> FEATURE:
<221> NAME/KEY: MOD_RES
<222> LOCATION: (4)..(4)
<223> OTHER INFORMATION: Orn

<400> SEQUENCE: 3

Lys Thr Thr Xaa Ser
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence:Oligopeptide
<220> FEATURE:
<221> NAME/KEY: MOD_RES
<222> LOCATION: (4)..(4)
<223> OTHER INFORMATION: Dbu

<400> SEQUENCE: 4

Lys Thr Thr Xaa Ser
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence:Oligopeptide
<220> FEATURE:
<221> NAME/KEY: MOD_RES
<222> LOCATION: (4)..(4)
<223> OTHER INFORMATION: Dpr

<400> SEQUENCE: 5

Lys Thr Thr Xaa Ser
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence:Oligopeptide
<220> FEATURE:
<221> NAME/KEY: MISC_FEATURE
<222> LOCATION: (2)..(3)
<223> OTHER INFORMATION: Xaa = allo-Thr

<400> SEQUENCE: 6

Lys Xaa Xaa Lys Ser
1               5

<210> SEQ ID NO 7
<211> LENGTH: 5
<212> TYPE: PRT
```

```
<213> ORGANISM: Artificial Sequence
<220> FEATURE:
<223> OTHER INFORMATION: Description of Artificial Sequence:Oligopeptide
<220> FEATURE:
<221> NAME/KEY: MISC_FEATURE
<222> LOCATION: (3)..(3)
<223> OTHER INFORMATION: Xaa = allo-Thr

<400> SEQUENCE: 7

Lys Thr Xaa Lys Ser
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence:Oligopeptide
      derivative
<220> FEATURE:
<221> NAME/KEY: MISC_FEATURE
<222> LOCATION: (1)..(1)
<223> OTHER INFORMATION: Xaa = Lipoyl-Lys(Lipoyl)
<220> FEATURE:
<221> NAME/KEY: MISC_FEATURE
<222> LOCATION: (4)..(4)
<223> OTHER INFORMATION: Xaa = Lys(Lipoyl)

<400> SEQUENCE: 8

Xaa Thr Thr Xaa Ser
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence:Oligopeptide
      derivative
<220> FEATURE:
<221> NAME/KEY: LIPID
<222> LOCATION: (1)..(1)
<223> OTHER INFORMATION: PALMITATE (N-2 linked)

<400> SEQUENCE: 9

Lys Thr Ser Lys Ser
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence:Oligopeptide
      derivative
<220> FEATURE:
<221> NAME/KEY: MISC_FEATURE
<222> LOCATION: (1)..(1)
<223> OTHER INFORMATION: Xaa = Octyl-1-sulfonyl-Lys
<220> FEATURE:
<221> NAME/KEY: MOD_RES
<222> LOCATION: (4)..(4)
<223> OTHER INFORMATION: Dbu

<400> SEQUENCE: 10

Xaa Ser Ser Xaa Ser
1               5

<210> SEQ ID NO 11
<211> LENGTH: 5
<212> TYPE: PRT
```

```
<213> ORGANISM: Artificial Sequence
<220> FEATURE:
<223> OTHER INFORMATION: Description of Artificial Sequence:Oligopeptide
      derivative
<220> FEATURE:
<221> NAME/KEY: MISC_FEATURE
<222> LOCATION: (1)..(1)
<223> OTHER INFORMATION: Xaa = Octylsulfonyl-Lys

<400> SEQUENCE: 11

Xaa Ser Ser Lys Ser
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence:Oligopeptide
<220> FEATURE:
<221> NAME/KEY: MOD_RES
<222> LOCATION: (4)..(4)
<223> OTHER INFORMATION: Orn

<400> SEQUENCE: 12

Lys Thr Ser Xaa Ser
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence:Protected
      oligopeptide
<220> FEATURE:
<221> NAME/KEY: MISC_FEATURE
<222> LOCATION: (1)..(1)
<223> OTHER INFORMATION: Xaa = Lys(Boc)
<220> FEATURE:
<221> NAME/KEY: MISC_FEATURE
<222> LOCATION: (2)..(2)
<223> OTHER INFORMATION: Xaa = Thr(tBu)
<220> FEATURE:
<221> NAME/KEY: MISC_FEATURE
<222> LOCATION: (3)..(3)
<223> OTHER INFORMATION: Xaa = Ser(tBu)
<220> FEATURE:
<221> NAME/KEY: MISC_FEATURE
<222> LOCATION: (4)..(4)
<223> OTHER INFORMATION: Xaa = Orn(Boc)
<220> FEATURE:
<221> NAME/KEY: MISC_FEATURE
<222> LOCATION: (5)..(5)
<223> OTHER INFORMATION: Xaa = Ser(tBu)

<400> SEQUENCE: 13

Xaa Xaa Xaa Xaa Xaa
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence:Oligopeptide
      derivative
<220> FEATURE:
<221> NAME/KEY: MISC_FEATURE
<222> LOCATION: (1)..(1)
<223> OTHER INFORMATION: Xaa = Octylsulfonyl-Lys
<220> FEATURE:
<221> NAME/KEY: MOD_RES
```

```
<222> LOCATION: (4)..(4)
<223> OTHER INFORMATION: Orn

<400> SEQUENCE: 14

Xaa Thr Ser Xaa Ser
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence:Oligopeptide
      derivative
<220> FEATURE:
<221> NAME/KEY: LIPID
<222> LOCATION: (1)..(1)
<223> OTHER INFORMATION: PALMITATE (N-2 linked)
<220> FEATURE:
<221> NAME/KEY: MOD_RES
<222> LOCATION: (4)..(4)
<223> OTHER INFORMATION: Dpr

<400> SEQUENCE: 15

Lys Thr Thr Xaa Ser
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence:Oligopeptide
      derivative
<220> FEATURE:
<221> NAME/KEY: LIPID
<222> LOCATION: (1)..(1)
<223> OTHER INFORMATION: PALMITATE (N-2 linked)
<220> FEATURE:
<221> NAME/KEY: MOD_RES
<222> LOCATION: (4)..(4)
<223> OTHER INFORMATION: Dbu

<400> SEQUENCE: 16

Lys Thr Thr Xaa Ser
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence:Oligopeptide
      derivative
<220> FEATURE:
<221> NAME/KEY: MISC_FEATURE
<222> LOCATION: (1)..(1)
<223> OTHER INFORMATION: Xaa = Laurinoyl-Lys
<220> FEATURE:
<221> NAME/KEY: MOD_RES
<222> LOCATION: (4)..(4)
<223> OTHER INFORMATION: Orn

<400> SEQUENCE: 17

Xaa Thr Thr Xaa Ser
1               5

<210> SEQ ID NO 18
<211> LENGTH: 5
<212> TYPE: PRT
<213> ORGANISM: Artificial Sequence
```

```
<220> FEATURE:
<223> OTHER INFORMATION: Description of Artificial Sequence:Oligopeptide
      derivative
<220> FEATURE:
<221> NAME/KEY: MISC_FEATURE
<222> LOCATION: (1)..(1)
<223> OTHER INFORMATION: Xaa = Myristinoyl-Lys
<220> FEATURE:
<221> NAME/KEY: MOD_RES
<222> LOCATION: (4)..(4)
<223> OTHER INFORMATION: Orn

<400> SEQUENCE: 18

Xaa Thr Thr Xaa Ser
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence:Oligopeptide
      derivative
<220> FEATURE:
<221> NAME/KEY: MISC_FEATURE
<222> LOCATION: (1)..(1)
<223> OTHER INFORMATION: Xaa = Stearinoyl-Lys
<220> FEATURE:
<221> NAME/KEY: MOD_RES
<222> LOCATION: (4)..(4)
<223> OTHER INFORMATION: Orn

<400> SEQUENCE: 19

Xaa Thr Thr Xaa Ser
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence:Oligopeptide
      derivative
<220> FEATURE:
<221> NAME/KEY: MISC_FEATURE
<222> LOCATION: (1)..(1)
<223> OTHER INFORMATION: Xaa = Palmitoleinyl-Lys
<220> FEATURE:
<221> NAME/KEY: MOD_RES
<222> LOCATION: (4)..(4)
<223> OTHER INFORMATION: Orn

<400> SEQUENCE: 20

Xaa Thr Thr Xaa Ser
1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence:Oligopeptide
      derivative
<220> FEATURE:
<221> NAME/KEY: MISC_FEATURE
<222> LOCATION: (1)..(1)
<223> OTHER INFORMATION: Xaa = Oleoyl-Lys
<220> FEATURE:
<221> NAME/KEY: MOD_RES
<222> LOCATION: (4)..(4)
<223> OTHER INFORMATION: Orn

<400> SEQUENCE: 21
```

```
Xaa Thr Thr Xaa Ser
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence:Oligopeptide
      derivative
<220> FEATURE:
<221> NAME/KEY: MISC_FEATURE
<222> LOCATION: (1)..(1)
<223> OTHER INFORMATION: Xaa = Eicosaenoyl-Lys
<220> FEATURE:
<221> NAME/KEY: MOD_RES
<222> LOCATION: (4)..(4)
<223> OTHER INFORMATION: Orn

<400> SEQUENCE: 22

Xaa Thr Thr Xaa Ser
1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence:Oligopeptide
      derivative
<220> FEATURE:
<221> NAME/KEY: LIPID
<222> LOCATION: (1)..(1)
<223> OTHER INFORMATION: PALMITATE (N-2 linked)
<220> FEATURE:
<221> NAME/KEY: MOD_RES
<222> LOCATION: (4)..(4)
<223> OTHER INFORMATION: Orn

<400> SEQUENCE: 23

Lys Thr Thr Xaa Thr
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence:Oligopeptide
      derivative
<220> FEATURE:
<221> NAME/KEY: LIPID
<222> LOCATION: (1)..(1)
<223> OTHER INFORMATION: PALMITATE (N-2 linked)
<220> FEATURE:
<221> NAME/KEY: MOD_RES
<222> LOCATION: (4)..(4)
<223> OTHER INFORMATION: Orn

<400> SEQUENCE: 24

Lys Ser Ser Xaa Ser
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence:Oligopeptide
      derivative
<220> FEATURE:
```

```
<221> NAME/KEY: MISC_FEATURE
<222> LOCATION: (1)..(1)
<223> OTHER INFORMATION: Xaa = Octadecyl-NH-CO-Lys
<220> FEATURE:
<221> NAME/KEY: MOD_RES
<222> LOCATION: (4)..(4)
<223> OTHER INFORMATION: Orn

<400> SEQUENCE: 25

Xaa Ser Ser Xaa Ser
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence:Oligopeptide
      derivative
<220> FEATURE:
<221> NAME/KEY: MISC_FEATURE
<222> LOCATION: (1)..(1)
<223> OTHER INFORMATION: Xaa = Hexadecyl-NH-CO-Lys
<220> FEATURE:
<221> NAME/KEY: MOD_RES
<222> LOCATION: (4)..(4)
<223> OTHER INFORMATION: Orn

<400> SEQUENCE: 26

Xaa Ser Ser Xaa Ser
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence:Oligopeptide
      derivative
<220> FEATURE:
<221> NAME/KEY: MISC_FEATURE
<222> LOCATION: (1)..(1)
<223> OTHER INFORMATION: Xaa = Tetradecyl-NH-CO-Lys
<220> FEATURE:
<221> NAME/KEY: MOD_RES
<222> LOCATION: (4)..(4)
<223> OTHER INFORMATION: Orn

<400> SEQUENCE: 27

Xaa Ser Ser Xaa Ser
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence:Oligopeptide
      derivative
<220> FEATURE:
<221> NAME/KEY: LIPID
<222> LOCATION: (1)..(1)
<223> OTHER INFORMATION: PALMITATE (N-2 linked)
<220> FEATURE:
<221> NAME/KEY: MOD_RES
<222> LOCATION: (4)..(4)
<223> OTHER INFORMATION: Orn

<400> SEQUENCE: 28

Lys Thr Thr Xaa Ser
1               5
```

```
<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence:Oligopeptide
      derivative
<220> FEATURE:
<221> NAME/KEY: LIPID
<222> LOCATION: (1)..(1)
<223> OTHER INFORMATION: PALMITATE (N-2 linked)
<220> FEATURE:
<221> NAME/KEY: MOD_RES
<222> LOCATION: (4)..(4)
<223> OTHER INFORMATION: Orn
<220> FEATURE:
<221> NAME/KEY: MOD_RES
<222> LOCATION: (5)..(5)
<223> OTHER INFORMATION: METHYLATION (N-2 linked)

<400> SEQUENCE: 29

Lys Thr Thr Xaa Ser
1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence:Oligopeptide
      derivative
<220> FEATURE:
<221> NAME/KEY: LIPID
<222> LOCATION: (1)..(1)
<223> OTHER INFORMATION: PALMITATE (N-2 linked)
<220> FEATURE:
<221> NAME/KEY: MOD_RES
<222> LOCATION: (4)..(4)
<223> OTHER INFORMATION: METHYLATION (N-2 linked), Orn

<400> SEQUENCE: 30

Lys Thr Thr Xaa Ser
1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence:Oligopeptide
      derivative
<220> FEATURE:
<221> NAME/KEY: LIPID
<222> LOCATION: (1)..(1)
<223> OTHER INFORMATION: PALMITATE (N-2 linked)
<220> FEATURE:
<221> NAME/KEY: MOD_RES
<222> LOCATION: (3)..(3)
<223> OTHER INFORMATION: METHYLATION (N-2 linked)
<220> FEATURE:
<221> NAME/KEY: MOD_RES
<222> LOCATION: (4)..(4)
<223> OTHER INFORMATION: Orn

<400> SEQUENCE: 31

Lys Thr Thr Xaa Ser
1               5

<210> SEQ ID NO 32
<211> LENGTH: 5
<212> TYPE: PRT
<213> ORGANISM: Artificial Sequence
```

```
<220> FEATURE:
<223> OTHER INFORMATION: Description of Artificial Sequence:Oligopeptide
      derivative
<220> FEATURE:
<221> NAME/KEY: LIPID
<222> LOCATION: (1)..(1)
<223> OTHER INFORMATION: PALMITATE (N-2 linked)
<220> FEATURE:
<221> NAME/KEY: MOD_RES
<222> LOCATION: (2)..(2)
<223> OTHER INFORMATION: METHYLATION (N-2 linked)
<220> FEATURE:
<221> NAME/KEY: MOD_RES
<222> LOCATION: (4)..(4)
<223> OTHER INFORMATION: Orn

<400> SEQUENCE: 32

Lys Thr Thr Xaa Ser
1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence:Oligopeptide
      derivative
<220> FEATURE:
<221> NAME/KEY: LIPID
<222> LOCATION: (1)..(1)
<223> OTHER INFORMATION: PALMITATE (N-2 linked)
<220> FEATURE:
<221> NAME/KEY: MOD_RES
<222> LOCATION: (1)..(1)
<223> OTHER INFORMATION: METHYLATION (N-2 linked)
<220> FEATURE:
<221> NAME/KEY: MOD_RES
<222> LOCATION: (4)..(4)
<223> OTHER INFORMATION: Orn

<400> SEQUENCE: 33

Lys Thr Thr Xaa Ser
1               5

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence:Oligopeptide
      derivative
<220> FEATURE:
<221> NAME/KEY: LIPID
<222> LOCATION: (1)..(1)
<223> OTHER INFORMATION: PALMITATE (N-2 linked)
<220> FEATURE:
<221> NAME/KEY: MISC_FEATURE
<222> LOCATION: (2)..(2)
<223> OTHER INFORMATION: Xaa = N-Et-Thr
<220> FEATURE:
<221> NAME/KEY: MOD_RES
<222> LOCATION: (4)..(4)
<223> OTHER INFORMATION: Orn

<400> SEQUENCE: 34

Lys Xaa Thr Xaa Ser
1               5

<210> SEQ ID NO 35
<211> LENGTH: 5
<212> TYPE: PRT
<213> ORGANISM: Artificial Sequence
<220> FEATURE:
```

```
<223> OTHER INFORMATION: Description of Artificial Sequence:Oligopeptide
      derivative
<220> FEATURE:
<221> NAME/KEY: LIPID
<222> LOCATION: (1)..(1)
<223> OTHER INFORMATION: PALMITATE (N-2 linked)
<220> FEATURE:
<221> NAME/KEY: MISC_FEATURE
<222> LOCATION: (2)..(2)
<223> OTHER INFORMATION: Xaa = N-Pr-Thr
<220> FEATURE:
<221> NAME/KEY: MOD_RES
<222> LOCATION: (4)..(4)
<223> OTHER INFORMATION: Orn

<400> SEQUENCE: 35

Lys Xaa Thr Xaa Ser
1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence:Oligopeptide
      derivative
<220> FEATURE:
<221> NAME/KEY: MISC_FEATURE
<222> LOCATION: (1)..(1)
<223> OTHER INFORMATION: Xaa = Octylsulfonyl-Lys
<220> FEATURE:
<221> NAME/KEY: MOD_RES
<222> LOCATION: (4)..(4)
<223> OTHER INFORMATION: Orn

<400> SEQUENCE: 36

Xaa Thr Thr Xaa Ser
1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence:Oligopeptide
      derivative
<220> FEATURE:
<221> NAME/KEY: MISC_FEATURE
<222> LOCATION: (1)..(1)
<223> OTHER INFORMATION: Xaa = Hexadecanylsulfonyl-Lys
<220> FEATURE:
<221> NAME/KEY: MOD_RES
<222> LOCATION: (4)..(4)
<223> OTHER INFORMATION: Orn

<400> SEQUENCE: 37

Xaa Thr Thr Xaa Ser
1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence:Oligopeptide
      derivative
<220> FEATURE:
<221> NAME/KEY: MISC_FEATURE
<222> LOCATION: (1)..(1)
<223> OTHER INFORMATION: Xaa = Pentdecafluoroheptyl-CO-Lys
<220> FEATURE:
<221> NAME/KEY: MOD_RES
<222> LOCATION: (4)..(4)
```

```
-continued

<223> OTHER INFORMATION: Orn

<400> SEQUENCE: 38

Xaa Thr Thr Xaa Ser
1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence:Oligopeptide
      derivative
<220> FEATURE:
<221> NAME/KEY: MOD_RES
<222> LOCATION: (4)..(4)
<223> OTHER INFORMATION: Orn
<220> FEATURE:
<221> NAME/KEY: MISC_FEATURE
<222> LOCATION: (5)..(5)
<223> OTHER INFORMATION: Xaa = Ser-O-Retinyl

<400> SEQUENCE: 39

Lys Thr Thr Xaa Xaa
1               5
```

DERMOPHARMACEUTICALLY AND COSMETICALLY ACTIVE OLIGOPEPTIDES

CROSS-REFERENCE TO RELATED APPLICATIONS

This application is the National Stage of International Application No. PCT/CH02/00587, filed May 8, 2003, which claims the benefit of Application No. CH 1986/01, filed Oct. 30, 2001, the contents of which is incorporated by reference herein.

FIELD OF THE INVENTION

The present invention relates to pharmaceutically, dermopharmaceutically and cosmetically active oligopeptides, to derivatives thereof, to peptide analogs and derivatives thereof as well as to the use thereof in dermopharmaceutically and cosmetically active compositions.

BACKGROUND OF THE INVENTION

The basic mechanism of skin aging is known to take place in the extracellular matrix, the so-called basal lamella, when situated at the intersection between epithelium and connective tissue. Regeneration of the extracellular matrix is highly important as it considerably influences the behaviour of those cells that are in contact with it, in particular their growth, migration, proliferation, form and functions. An age-related reduction of collagen synthesis by fibroblasts occurs in this extracellular matrix, the consequence of which being a reduced number of chemical substances secreted by these cells. As skin proteins consist by approx. 80% of collagen, already a small natural decrease of the collagen concentration in the tissue may have clear consequences on the mechanical and physiological properties of skin.

Katayama et al. (The Journal of Biological Chemistry, Vol. 268, No. 14, pages 9941-9944, 1993) found that the minimal subfragment sequence for stimulating collagen and fibronectin is represented by the pentapeptide Lys-Thr-Thr-Lys-Ser. Sequences with four amino acids or less have a slighter or no stimulating effect.

The European patent application WO 00/15188 describes the effect of the palmitoylated pentapeptide Palm-Lys-Thr-Thr-Lys-Ser as a component for treating skin aging, accelerating wound healing and improving skin moisturizing.

SUMMARY OF THE INVENTION

It has been found that selected, new oligopeptides and derivatives thereof as well as peptide analogs and derivatives thereof (in the following referred to as "compounds of the present invention") are surprisingly highly pharmaceutically and/or cosmetically effective and are particularly appropriate for use in dermopharmaceutically and/or cosmetically effective compositions. The compounds of the present invention diffuse rapidly and in sufficient concentration through the cell membrane up to the intracellular site of action, where they lead to a clearly increased production of collagen and fibronectin. Thus, the compounds of the present invention exert a surprisingly positive and stimulating effect on the extracellular matrix which decisively influences the mechanical and physiological appearance of skin. In particular, the compounds of the present invention induce a much more rapid and stronger stimulation of collagen synthesis than known so far for other compounds from the state of the art. The quicker and stronger stimulation of collagen synthesis by the compounds of the present invention is probably the result of a synergic effect which is obtained by reduction of the molecular mass, introduction of N-methyl groups in amino acids and modification of amino acids with, e.g., fatty acid esters. However, the present invention is not bound to this explanation.

DETAILED DESCRIPTION OF PREFERRED EMBODIMENTS

The present invention is defined in the claims and relates in particular to selected, new oligopeptides and derivatives thereof, peptide analogs and derivatives thereof, as well as pharmaceutically acceptable salts of these compounds, thereby characterized that these compounds correspond to general formula (I)

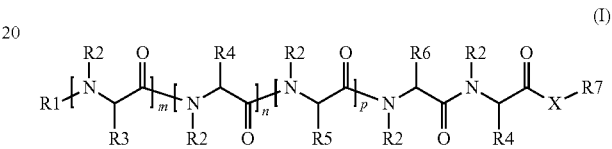

wherein $R^1$ represents H, —C(O)—$R^7$, —$SO_2$—$R^7$, —C(O)—$OR^7$ or —C(O)—N($R^7$)$_2$, $R^2$ represents, independent of one another, H or —($C_1$-$C_4$)-alkyl, $R^3$, $R^6$ represent, independent of one another, —$(CH_2)_q$—N($R^1$)$R^8$, $R^4$, $R^5$ represent, independent of one another, —$CH_2$—$OR^2$, —CH($CH_3$)$OR^8$ or —$CH_2$—$CH_2$—$OR^8$, $R^7$ represents hydrogen, ($C_1$-$C_{19}$)-alkyl optionally substituted once or several times, independent of one another, with halogen, hydroxy, carboxyl, amino, mercapto, 1,2-dithiolanyl, and/or sulfo; optionally substituted ($C_1$-$C_{19}$)-alkenyl; phenyl-($C_1$-$C_4$)-alkyl, whose phenyl radical is optionally substituted with amino in the para position; or $R^8$ represents H, —($C_1$-$C_4$)-alkyl, —C(O)—$R^7$, —C(O)—$OR^7$, —C(O)—N($R^7$)$_2$ or —$SO_2$—$R^7$ X represents oxygen (—O—) or —NH—; or $XR^7$, with X=O, also represents the esters of α-tocopherol, tocotrienol or retinol or the carboxylic acid (with $R^7$=H), m, n, p represent, independent of one another, zero or 1 and q in $R^3$ and $R^6$ represents, independent of one another, an integer from 1 to 4, with the provision that the following conditions do not simultaneously occur: $R^4$=—CH($CH_3$)—OH and $R^5$=—CH($CH_3$)—OH and $R^6$=—$(CH_2)_4$—$NH_2$.

Preferably, the following conditions do not simultaneously occur: $R^4$=—$CH_2$—OH or —CH($CH_3$)—OH and $R^5$=—CH($CH_3$)—OH and $R^6$=—$(CH_2)_4$—$NH_2$. Preferably, the following conditions do not simultaneously occur: $R^2$=H and $R^4$=—$CH_2$—OH or —CH($CH_3$)—OH and $R^5$=—CH($CH_3$)—OH and $R^6$=—$(CH_2)_4$—$NH_2$.

The compounds of formula (I) comprise dipeptides, tripeptides, tetrapeptides and pentapeptides of the corresponding amino acids and derivatives thereof according to the definitions of $R^1$, $R^2$, $R^7$ and $R^8$, as well as corresponding peptide analogs.

The amino acid residues in general formula (I), which contain the substituents $R^3$ or $R^6$, are derived from lysine (Lys), ornithine (Orn), 2,4-diaminobutyric acid (Dab) or 2,3-diaminopropionic acid (Dap) and are residues of these amino acids or amino acid derivatives.

The amino acid residues in general formula (I), which contain the substituents $R^4$ or $R^5$, are derived from serine (Ser), threonine (Thr), homoserine [$H_2N$—$CH((CH_2)_2$—$OH)COOH$, (HSe)] and are residues of these amino acids or amino acid derivatives.

The following table shows from which amino acids the compounds of the above formula (I) are derived:

| $R^1(N(R^2)CH(R^3)C(O)$ derived from: | $N(R^2)CH(R^4)C(O)$ derived from: | $N(R^2)CH(R^5)C(O)$ derived from: | $N(R^2)CH(R^6)C(O)$ derived from: | $N(R^2)CH(R^4)C(X)R^7$ derived from: |
|---|---|---|---|---|
| Lysine (Lys) | Serine (Ser) | Serine (Ser) | Lysine (Lys) | Serine (Ser) |
| Ornithine (Orn) | Homoserine (HSe) | Homoserine (HSe) | Ornithine (Orn) | Homoserine (HSe) |
| 2,4-Diaminobutyric acid (Dab) | Threonine (Thr) | Threonine (Thr) | 2,4-Diaminobutyric acid (Dab) | Threonine (Thr) |
| 2,3-Diaminopropionic acid (Dap) | | | 2,3-Diaminopropionic acid (Dap) | |

The residue [$R^1(N(R^2)CH(R^3)C(O)$—] is preferably derived from lysine.

The residue [—$N(R^2)CH(R^4)C(O)$—] at position [—$N(R^2)CH(R^4)C(O)$—$N(R^2)CH(R^5)C(O)$—] is preferably derived from threonine.

The residue [—$N(R^2)CH(R^5)C(O)$—] is preferably derived from threonine.

The residue [—$N(R^2)CH(R^6)C(O)$—] is preferably derived from ornithine, 2,4-diaminobutyric acid (Dab), and 2,3-diaminopropionic acid (Dap).

The terminal residue [—$(N(R^2)CH(R^4)C(O)$—$XR^7$] is preferably derived from serine.

The compounds of formula (I) preferably contain the following sequences:

```
Sequence 1:        -Ser-Ser-Orn-

Sequence 2:        -Thr-Thr-Orn-

Sequence 3:        -Thr-Thr-Dab-

Sequence 4:        -Thr-Thr-Dap-
```

The compounds with the sequences -Ser-Ser-Orn-, Lys-Thr-Thr-Orn-Ser, Lys-Thr-Thr-Dab-Ser and Lys-Thr-Thr-Dab-Ser, as well as the sequences correspondingly derivatized with the substituents $R^1$, $R^2$, $R^7$ and $R^8$ are particularly preferred.

Further preferred polypeptides enclosed by formula (I) are mentioned in the text.

Preferred compounds of formula (I) are also those wherein m=zero, when n or p=zero.

The terms "peptides" and "oligopeptides" above all comprise naturally occurring amino acids, peptides and oligopeptides, respectively. Peptide analogs mean synthetically modified amino acids, peptides and oligopeptides, respectively, e.g. with a methyl group at the nitrogen atom ($CH_3$—N=). Derivatives within the present invention particularly mean amino acids, peptides and oligopeptides, respectively, the terminal amino group or carboxyl group of which has been further converted, e.g. wherein the terminal carboxyl group has been esterified.

The compounds of formula (I) are particularly appropriate as pharmaceutical, dermopharmaceutical and/or cosmetic active ingredients for the preparation of pharmaceutically, dermopharmaceutically and/or cosmetically active compositions, in particular for increasing the collagen and fibronectin production in human skin.

Moreover, the present invention relates to a method for preparing the compounds of the present invention and salts thereof and their use as pharmaceutical, dermopharmaceutical and/or cosmetic active ingredients, as well as pharmaceutically, dermopharmaceutically and/or cosmetically active compositions which contain at least one compound of the present invention.

Furthermore, the present invention relates to the use of the compounds of the present invention for preparing a wound healing- and moisturizing-stimulating drug as well as to a method for delaying or treating skin aging, in particular the formation of wrinkles, which comprises applying a compound of the present invention and/or a composition of the present invention on the skin.

The above used, general terms are defined as follows:

Halogen means chlorine, bromine or iodine, preferably fluorine.

Alkyl, as a group per se or as a structural element of an alkoxy function, comprises linear as well as branched alkyl groups. Examples thereof are methyl, ethyl, propyl, n-butyl, n-pentyl, n-hexyl, n-heptyl, n-octyl, n-nonyl, n-undecanyl, n-dodecanyl, n-tridecanyl, n-hexadecanyl, n-heptadecanyl, n-octadecanyl or n-nonadecanyl as unbranched residues and isopropyl, tert.butyl, isobutyl, sec.butyl, isoamyl as branched residues. $R^2$ and/or $R^8$ as alkyl preferably means methyl, ethyl and propyl, preferably methyl. If $R^7$ as a part of $R^1$ means or contains an alkyl residue, it preferably represents alkyl with 8 to 22 C atoms, preferably with 14 to 17 C atoms. If $XR^7$ contains an alkyl residue, it preferably means alkyl with 1 to 22 C atoms, preferably with 1 to 4 C atoms.

Alkenyl has the denotation of a mono- or poly-unsaturated, optionally substituted alkyl group, such as e.g. 8(Z)-heptadecenyl, 8(Z),11(Z)-heptadecadienyl, 4(Z),7(Z),10(Z), 13(Z)-nonadecatetraenyl, 8(Z)-11-hydroxyoctadecenyl.

α-Tocopheryl means (D)-, (L)- or (DL)-2,5,7,8-tetramethyl-2-(4',8',12'-trimethyltridecyl)-6-chromanyl. Tocotrienyl means any isomer of 2,5,7,8-tetramethyl-2-(4',8',12'-trimethyl-3',7',11'-tridecatrienyl)-6-chromanyl. Retinyl means 3,7-dimethyl-9-(2,6,6-trimethyl-1-cyclohexenyl)-2,4,6,8-nonatetraen-1-yl.

The compounds of formula (I) together with acids can form mono- or polyvalent, homogeneous or mixed salts, e.g. with inorganic acids, such as hydrochloric acid, bromhydric acid, sulfuric acid or phosphoric acid; or with appropriate organic aliphatic saturated or unsaturated carboxylic acids, e.g. aliphatic mono- or dicarboxylic acids, such as formic acid, acetic acid, trifluoroacetic acid, trichloroacetic acid, propionic acid, glycolic acid, succinic acid, fumaric acid, malonic acid, maleic acid, oxalic acid, phthalic acid, citric acid, lactic acid or tartaric acid; or with aromatic carboxylic acids, such as benzoic acid or salicylic acid; or with aromatic-aliphatic carboxylic acids, such as mandelic acid or cinnamic acid; or with heteroaromatic carboxylic acids, such as nicotinic acid; or with aliphatic or aromatic sulfonic acids, such as methanesulfonic acid or toluenesulfonic acid. Dermatologically tolerated salts, in particular salts with acetic acid and/or lactic acid, are preferred.

The compounds of general formula (I) also comprise the possible isomeric forms as well as mixtures thereof, e.g. racemic mixtures and mixtures of rotamers.

The amino acids mentioned in formula (I) can have an L or D configuration, or represent a mixture of both configurations.

In particular, Thr may also represent the isomeric forms allo-Thr, D-Thr or D-allo-Thr or a mixture of Thr with D-Thr or allo-Thr with D-allo-Thr at the respective position in the sequence.

Among the compounds of formula (I), the following denotations or the following groups of compounds, respectively, are preferred, wherein $R^1$ represents hydrogen, —C(O)—$R^7$, —SO$_2$—$R^7$, —C(O)—OR$^7$ or —C(O)—N($R^7$)$_2$, preferably wherein $R^1$ represents hydrogen, —C(O)—$R^7$ or —SO$_2$—$R^7$, preferably hydrogen or —C(O)—$R^7$ $R^2$ represents, independent of one another, hydrogen or methyl $R^3$, $R^6$ represent, independent of one another, —(CH$_2$)$_q$—N($R^1$)$R^8$, preferably, independent of one another, —(CH$_2$)$_q$—NH$_2$.

$R^4$, $R^5$ represent, independent of one another, —CH$_2$—OR$^8$, —CH(CH$_3$)OR$^8$ or —CH$_2$—CH$_2$—OR$^8$, preferably, independent of one another, —CH$_2$—OH, —CH(CH$_3$)OH or —CH$_2$—CH$_2$—OH, $R^7$ preferably represents hydrogen, methyl, ethyl, propyl, n-butyl, n-pentyl, n-hexyl, n-heptyl, n-octyl, n-nonyl, n-undecanyl, n-dodecanyl, n-tridecanyl, n-tetradecanyl, n-pentadecanyl, n-hexadecanyl, n-heptadecanyl, n-octadecanyl or n-nonadecanyl, isopropyl, tert.butyl, isobutyl, sec.butyl, isoamyl, phenyl, t-butylphenyl, tolyl, 1- or 2-naphthyl, perfluorobutyl, pentadecafluoroheptyl, (+)- or (−)-bornan-2-onyl, 8(Z)-heptadecenyl, 8(Z),11(Z)-heptadecadienyl, 4(Z),7(Z),10(Z),13(Z)-nonadecatetraenyl or 8(Z)-11-hydroxyoctadecenyl, 1,2-dithiolanyl or $C_1$-$C_{19}$-alkyl substituted with amino in ω position, or phenyl optionally substituted with methyl, amino or halogen in ortho- and/or para position, preferably $R^7$ as a part of XR$^7$ represents hydrogen, methyl, ethyl and/or $R^7$ as a part of $R^1$ represents an alkyl residue with 14 to 17 C atoms.

$R^8$ represents hydrogen, $C_1$-$C_4$-alkyl or —C(O)—$R^7$, preferably hydrogen or methyl.

X represents oxygen, —NH—, preferably oxygen,

XR$^7$, with X=O, also represents the esters of α-tocopherol, tocotrienol or retinol or the carboxylic acid (with $R^7$=H), preferably the carboxylic acid, m, n, p represent, independent of one another, zero or 1, and q in $R^3$ and $R^6$ represents, independent of one another, the integer 1, 2, 3 or 4.

$R^7$—C(O)— most preferably represents the residue of a saturated or unsaturated fatty acid with 6, 8, 10, 12, 14, 16 or 18 C atoms, preferably the corresponding residue of a saturated fatty acid, preferably the corresponding residue of caprylic acid [CH$_3$—(CH$_2$)$_6$—C(O)—], lauric acid [CH$_3$—(CH$_2$)$_{10}$—C(O)—], myristic acid [CH$_3$—(CH$_2$)$_{12}$—C(O)—], palmitic acid [CH$_3$—(CH$_2$)$_{14}$—C(O)—] and/or stearic acid [CH$_3$—(CH$_2$)$_{16}$—C(O)—].

Representative examples of compounds of formula (I) are listed in Table 5 (after Example 7).

The compounds of the present invention can be manufactured according to methods known per se in peptide chemistry. The preferred procedure comprises fully assembling the compound of the present invention, e.g. a compound of formula (I), optionally splitting off the remaining protective group(s) and optionally acylating a free amino group and/or converting the obtained compound into an acid addition salt and/or an obtained acid addition salt into the corresponding conjugate base or into another salt.

The compounds of the present invention can be used for the preparation of a dermopharmaceutically and/or cosmetically active composition. Such compositions contain an effective quantity of at least one compound of the present invention or a salt thereof, in the range from 0.5 ppm to 5,000 ppm (w/w), preferably between 1 ppm and 1000 ppm (w/w), calculated on the weight of the compound of the present invention and of the bulking agent(s). The compounds of the present invention can be used as a solution, a dispersion, an emulsion or encapsulated in carriers, such as e.g. in macro-, micro- or nanocapsules, in liposomes or chylomicrons, or enclosed in macro-, micro- or nanoparticles or in microfungi or adsorbed on powdered organic polymers, talc, bentonite and further inorganic carriers.

The compounds of the present invention can be used in any galenic form, such as emulsions, milks, lotions, ointments, gelatinous and viscous, lifting and emulsifying polymers, pomades, shampoos, soaps, gels, powders, sticks, sprays, body oils, face masks or a plaster for transdermal application.

The compounds of the present invention can be used with any further, commonly used ingredient, such as extraction lipids and/or synthetic lipids, gelatinous and viscous, lifting and emulsifying polymers, water- or fat-soluble active agents, plant extracts, tissue extracts, marine extracts, sun-protective agents, antioxidants, water-retaining and barrier substances as well as skin-revitalizing agents.

The compounds of the present invention are used in cosmetic applications to enhance wound healing and hydration, and in all skin care products, in particular against the formation and aggravation of wrinkles and against all consequences of natural or accelerated (sun rays, pollution) skin aging.

The compounds of the present invention as well as the cosmetic and dermopharmaceutical compositions containing same can be used for the preparation of a drug to promote wound healing and hydration, and for all skin care products, in particular against the formation and aggravation of wrinkles and against all consequences of natural or accelerated (sun rays, pollution) skin aging.

The present invention also relates to a method for delaying or treating skin aging, in particular wrinkle formation, which comprises the application on the skin of a compound of the present invention. Analogously, the present invention relates to a method for accelerating wound healing and/or improving skin hydration, which comprises the application on the skin of a compound of the present invention.

The following examples illustrate the invention without limiting its scope. The following abbreviations are used in the text and in Examples 1-7:

AcOH: Acetic acid
Boc: tert.-Butyloxycarbonyl
Dab: 2,4-Diaminobutyric acid
Dap: 2,3-Diaminopropionic acid
DBU: 1,8-Diazabicyclo[5,4,0]undec-7-ene(1,5-5)
DIPEA: Diisopropylethylamine
DMEM: Dulbecco's Modified Eagle Medium
Et: Ethyl
FCS: Fetal Calf Serum
HSe: Homoserine
Hyp: Hydroxyproline
Gly: Glycine
Lipoyl: α-D,L-Lipoic acid
Me: Methyl
MEM: Minimal Essential Medium
N-Me-Ser: N-Methyl-Serine
N-Me-Thr: N-Methyl-Threonine
NMM: N-Methylmorpholine
Orn: Ornithine
Palm: Palmitoyl
PBS: Phosphate buffered saline
Pr: Propyl
RT: Room temperature
TBTU: O-(Benzotriazol-1-yl)-N,N,N',N'-tetramethyluronium-tetrafluoroborate
tBu: t-Butyl
TFA: Trifluoroacetic acid
TGF-β(beta)1: Transforming Growth Factor-beta(β)

Example 1

Determination of the Stimulation of Collagen Synthesis Type I+III in Fibroblast Cell Cultures (ATCC CCL110) by Treatment with the Oligopeptide Derivatives of the Present Invention Method:
The collagen I and III content in fibroblasts is measured with the Sirius Red microassay. The quantitative determination of collagen is carried out after 24 hours of incubation with the corresponding oligopeptide derivatives. The extracellularly accumulated collagen is determined. Vitamin C and TGF-beta-1 are used as positive controls.

Method:
ATCC CCL110 fibroblasts are incubated in culture medium at a density of approx. 125,000 cells/well in 6-well cell culture plates for 2 days (37° C./5% $CO_2$). Afterwards, the medium is discarded and washed twice with PBS, whereupon 1 ml of test medium with corresponding test substances is added. After incubation with test substance under culture conditions (37° C./5% $CO_2$) for further 24 hours, the extracellular collagen is measured with the Sirius Red assay.

Sirius Red Assay Extracellular:
After the incubation period, the total volume of test medium (1 ml) is transferred into a flat-bottom 24-well plate and dried overnight at 55° C. The samples are fixed with 1 ml/well of Bouin's fluid for 1 hour at room temperature (RT). The fixing solution is discarded and the plates are washed 2-3 times with water. After drying of the plates, 1 ml of Sirius Red dye reagent is added.
The samples are shaken for 1 hour at RT on a microplate agitator at moderate intensity. Afterwards, the Sirius Red dye reagent is discarded and the plates are washed with 0.01N HCl. The tinted material is dissolved in 0.3 ml of 0.1N NaOH solution and shaken on a microplate agitator for 1 hour at RT.
200 µl of solution is transferred into a flat-bottom 96-well plate and the optical density is measured at 540 nm against 0.1N NaOH solution as the blank.

Material:
Culture medium: MEM+10% FCS+100 IU/ml penicillin+0.1 mg/ml streptomycin+1 mM non essential amino acids+1 mM Na-pyruvate+2 mM L-glutamine.
Test medium: DMEM without phenol red (AMIMED)+100 IU/ml penicillin+0.1 mg/ml streptomycin+80 µg/ml beta (β)-aminopropionitrile.

Dilution of the Substances:
Vitamin C 100 mM (SIGMA A4034) is diluted to 50 µg/ml in the test medium.
Transforming growth factor TGFβ1 1 µg/ml (SIGMA T1654) is diluted to 0.1 ng/ml in the test medium.
The oligopeptide derivatives of the present invention are prepared in a regular concentration of 10 mM and diluted to 50 µM in the test medium.

Reagents for the Sirius Red Microassay:
Sirius Red F3BA dye reagent as the stock solution 1 mg/ml in saturated aqueous picric acid solution. Bouin's fluid: 15 ml of saturated aqueous picric acid solution+5 ml of formaldehyde+1 ml of acetic acid. The results are shown in Table 1.

TABLE 1

Results, quantitative determination of collagen type I + III after 24 hours:

| Test substance at a concentration of 50 µM except where otherwise stated | Extracellular |
|---|---|
| Control without active | 100% |
| TGFβ1 0.1 ng/ml | 115% |
| Vitamin C | 128% |
| H-Dab-Ser-OH × 2 TFA | 131% |
| H-Lys-allo-Thr-allo-Thr-Lys-Ser-OH × 3 AcOH | 139% |
| H-Lys-Thr-allo-Thr-Lys-Ser-OH × 3 AcOH | 134% |
| H-Lys-Thr-Thr-Dab-Ser-OH × 3 AcOH | 137% |
| Lipoyl-Lys (Lipoyl)-Thr-Thr-Lys (Lipoyl)-Ser-OH | 162% |
| Palm-Lys-Thr-Ser-Lys-Ser-OH | 128% |

Example 2

Determination of the Fibronectin Content after Treatment with the Oligopeptide Derivatives of the Present Invention Method:
The fibronectin (laminin or collagen VII) content in the fibroblast cells is determined by immuno-dot blotting. Cultivation and incubation of the cells are carried out in the same way as described in Example 1. Afterwards, the cells are lysed and the lysates (0.5 ml) are blotted on a nitrocellulose sheet in a prepared bio-dot device. The sheets are then incubated with a specific primary antibody to human fibronectin according to the western blotting method. A conjugate with alkaline phosphatase is used as the secondary antibody. The intensity of the bands is visually determined semi-quantitatively after dying and stopping of the reaction. The results are shown in Table 2.

TABLE 2

Results, quantitative determination of fibronectin (or laminin V or collagen type VII) after 24 hours of incubation:

| Test substance, at a concentration of 50 µM except where otherwise stated | Extracellular (relative dyeing intensity) |
|---|---|
| Control without active | ++ |
| TGFβ1 0.1 ng/ml | ++ |
| Vitamin C | +++(+) |
| H-Dab-Ser-OH × 2 TFA | ++++ |
| H-Lys-allo-Thr-allo-Thr-Lys-Ser-OH × 3 AcOH | ++++ |
| H-Lys-Thr-Thr-Dab-Ser-OH × 3 AcOH | ++++ |
| H-Lys-allo-Thr-Lys-Ser-OH × 3 AcOH | +++(+) |
| Lipoyl-Lys (Lipoyl)-Thr-Thr-Lys (Lipoyl)-Ser-OH | ++++++ |
| Palm-Lys-Thr-Ser-Lys-Ser-OH | +++(+) |

Example 3

Formulation of an Ointment

Method: Ingredients 1-5 (A) are heated to 70° C. Ingredients 6-7 (B) are heated to 75° C. Under stirring B is added to A, cooled to 50° C., homogenized and cooled to 30° C. Afterwards, ingredients 8-9 (C) and ingredient 10 (D) are added one after the other and stirred cold. The formulations are shown in Table 3.

TABLE 3

| Number | Ingredient | | % w/w |
|---|---|---|---|
| 1 | (A) | Tego Care 450 | 3.00 |
| 2 | | Cetearylalcohol | 2.25 |
| 3 | | Glycerylstearate | 2.25 |
| 4 | | Cetiol 868 | 10.00 |
| 5 | | Squalane | 5.00 |
| 6 | (B) | Deionized water | 66.995 |
| 7 | | Sodium hyaluronate | 5.00 |
| 8 | (C) | Glycerin | 5.00 |
| 9 | | Phenonip | 0.5 |
| 10 | (D) | Octyl-1-SO$_2$-Lys-Ser-Ser-Dab-Ser-OH | 0.005 |

Example 4

Formulation of a Gel

Method: Ingredients 2-6 (A) are dissolved one after the other in deionized water. After adjusting the pH to 6.0 with ingredient 7 (B), ingredient 8 (C) is added. The formulations are shown in Table 4.

TABLE 4

| Number | Ingredient | | % w/w |
|---|---|---|---|
| 1 | (A) | Deionized water | 92.095 |
| 2 | | 1,3-Butanediol | 5.00 |
| 3 | | Phenonip | 0.50 |
| 4 | | Abil B 8843 | 1.50 |
| 5 | | Carboxymethyl Cellulose | 0.15 |
| 6 | | Carbopol Ultrez 10 | 0.75 |
| 7 | (B) | NaOH | |
| 8 | (C) | Octyl-SO$_2$-Lys-Ser-Ser-Lys-Ser-OH | 0.005 |

Examples 5-7

The following embodiments 5-7 describe the synthesis of the compounds of formula (I) of the present invention and of salts of such compounds. The eluates and products obtained according to the examples are analysed using proton NMR, HPLC-electrospray MS or elementary analysis. The compounds can be manufactured according to known methods described hereinafter (general instructions from M. Bodanszky "The Practice of Peptide Synthesis", Springer, $2^{nd}$ Edition, 1994). Accordingly, the amino acid, e.g. serine, is bound to a resin at the carboxy terminal end in a solid-phase synthesis, whereby its amino group is protected by a protective group, e.g. by the Fmoc protective group. The side chain is protected with, e.g., Boc or t-butyl. If necessary, the protective groups are selectively split off in order to link up the further amino acid derivatives with the reagents commonly used in peptide synthesis until the desired chain is completely built up. Afterwards, the peptide or peptide analog, respectively, is split off from the resin at the carboxy terminal end and this carboxy terminal end is connected with varying $C(O)-R^7$, $SO_2-R^7$, $C(O)-OR^7$ or $C(O)-N(R^7)_2$ residues, whereupon the protective groups are removed.

Example 5

H-Lys-Thr-Ser-Orn-Ser×3 TFA

Synthesis of H-Lys(Boc)-Thr(tBu)-Ser(tBu)-Orn(Boc)-Ser(tBu)-OH×TFA (5a):

In a typical solid-phase synthesis protocol, the pentapeptide is obtained by repetitive coupling of 18.7 g (14.0 mmol, charge: 0.75 mmol/g) of commercial H-Ser(tBu)-chlorotrityl resin with 16.8 mmol of the amino acids Fmoc-Orn(Boc)-OH, Fmoc-Thr(tBu)-OH (2×), Fmoc-Lys(Boc)-OH, 18 mmol TBTU, 33.6 mmol collidin and unblocking with 1% DBU in DMF (2×5 min), splitting from the resin with 1% TFA in dichloromethane and purification over Sephadex LH20®, yield: 9.3 g (64%).

Synthesis of H-Lys-Thr-Ser-Orn-Ser-OH×3TFA (5b):

9.3 g of 5a is stirred for 1 hour at RT in a mixture composed of 59 ml of TFA, 1.25 ml of water and 1.25 ml of triisopropylsilan. After reduction to ⅓ of the volume, precipitation with diethylether is carried out, yield: 6.0 g (76%).

Example 6

Synthesis of $CH_3-(CH_2)_7-SO_2$-Lys-Thr-Ser-Orn-Ser×2 TFA (6):

2 g (2.2 mmol) of 5a is dissolved in DMF (20 ml) and stirred with 0.48 g (2.3 mmol) of 1-octanesulfochloride and 0.48 g (4.0 mmol) of DIPEA for 10 h at RT. After evaporation of the solvent, the crude product is stirred with 59 ml of TFA, 1.25 ml of water and 1.25 ml of triisopropylsilan for 1 h at RT. After reduction to ⅓ of the volume, precipitation with diethylether and purification over Sephadex LH20® are carried out, yield: 1.4 g (70%).

The peptide or conjugate can also be protonized with an inorganic acid, e.g. HCl, HBr, $H_2SO_4$ or $H_3PO_4$, or with an organic acid, e.g. formic acid, oxalic acid or tartaric acid, leading to corresponding salts of 6.

Example 7

H-Dab-Ser-OH×2 AcOH

According to the described solid-phase protocol from Example 5a, the obtained H-Dab-Ser-OH×2 TFA (3.0 g, 6.90 mmol) is analogously transformed in the acetate salt over an ion exchanger, yield 2.0 g (90.0%).

The following compounds can also be synthesized according to the methods described in Examples 5-7:

TABLE 5

| No | Sequence | ESI-MS |
|---|---|---|
| 1 | H-Dap-Ser-OH × 2TFA | 192.1 |
| 2 | Palm-Orn-Ser-OH × TFA | 458.5 |
| 3 | Palm-Orn-N-Me-Ser-OH × TFA | |
| 4 | Palm-Dab-Ser-OH × TFA | 444.3 |
| 5 | Laurinoyl-Lys-Ser-OH × TFA | 416.5 |
| 6 | Palm-Lys-Ser-OH × TFA | 472.7 |
| 7 | Oleoyl-Lys-Ser-OH × TFA | 498.6 |
| 8 | Palm-Lys-Thr-Thr-Dap-Ser-OH × 2AcOH | 760.8 |
| 9 | Palm-Lys-Thr-Thr-Dab-Ser-OH × 2AcOH | 775.0 |
| 10 | Laurinoyl-Lys-Thr-Thr-Orn-Ser-OH × 2AcOH | 732.8 |
| 11 | Myristinoyl-Lys-Thr-Thr-Orn-Ser-OH × 2AcOH | 760.8 |
| 12 | Stearinoyl-Lys-Thr-Thr-Orn-Ser-OH × 2AcOH | 817.1 |
| 13 | Palmitoleinoyl-Lys-Thr-Thr-Orn-Ser-OH × 2AcOH | 787.1 |

TABLE 5-continued

| No | Sequence | ESI-MS |
|---|---|---|
| 14 | Oleoyl-Lys-Thr-Thr-Orn-Ser-OH × 2AcOH | 815.0 |
| 15 | Eicosaenoyl-Lys-Thr-Thr-Orn-Ser-OH × 2AcOH | 843.1 |
| 16 | Palm-Lys-Thr-Thr-Orn-Thr-OH × 2AcOH | 803.1 |
| 17 | Palm-Lys-Ser-Ser-Orn-Ser-OH × 2AcOH | 761.0 |
| 18 | Octadecyl-NH-C(O)-Lys-Ser-Ser-Orn-Ser-OH × 2AcOH | 846.1 |
| 19 | Hexadecyl-NH-C(O)-Lys-Ser-Ser-Orn-Ser-OH × 2AcOH | 818.1 |
| 20 | Tetradecyl-NH-C(O)-Lys-Ser-Ser-Orn-Ser-OH × 2AcOH | 790.1 |
| 21 | Palm-Lys-Thr-Thr-Orn-Ser-OH × 2AcOH | 788.9 |
| 22 | Palm-Lys-Thr-Thr-Orn-N-Me-Ser-OH × 2AcOH | |
| 23 | Palm-Lys-Thr-Thr-N-Me-Orn-Ser-OH × 2AcOH | |
| 24 | Palm-Lys-Thr-N-Me-Thr-Orn-Ser-OH × 2AcOH | |
| 25 | Palm-Lys-N-Me-Thr-Thr-Orn-Ser-OH × 2AcOH | |
| 26 | Palm-N-Me-Lys-Thr-Thr-Orn-Ser-OH × 2AcOH | |
| 27 | Palm-Lys-N-Et-Thr-Thr-Orn-Ser-OH × 2AcOH | |
| 28 | Palm-Lys-N-Pr-Thr-Thr-Orn-Ser-OH × 2AcOH | |
| 29 | $C_8H_{17}$-$SO_2$-Lys-Thr-Thr-Orn-Ser-OH × 2AcOH | 726.8 |
| 30 | $C_{16}H_{33}$-$SO_2$-Lys-Thr-Thr-Orn-Ser-OH × 2AcOH | 839.1 |
| 31 | $C_7F_{15}$-C(O)-Lys-Thr-Thr-Orn-Ser-OH × 2AcOH | 946.8 |
| 32 | H-Lys-Thr-Thr-Orn-Ser-ORetinyl 3 × 2AcOH | |

What is claimed is:

1. A composition comprising an acetate salt selected from the group consisting of:
   Octadecyl-NH—C(O)-Lys-Ser-Ser-Orn-Ser-OH×2AcOH,
   Hexadecyl-NH—C(O)-Lys-Ser-Ser-Orn-Ser-OH×2AcOH,
   Tetradecyl-NH—C(O)-Lys-Ser-Ser-Orn-Ser-OH×2AcOH, and
   Palm-Lys-Ser-Ser-Orn-Ser-OH×2AcOH.

2. A composition comprising an acetate salt selected from the group consisting of:
   Palm-Lys-Thr-Thr-Dap-Ser-OH×2AcOH and
   Palm-Lys-Thr-Thr-Dab-Ser-OH×2AcOH.

3. A composition comprising an acetate salt selected from the group consisting of:
   Laurinoyl-Lys-Thr-Thr-Orn-Ser-OH×2AcOH,
   Myristinoyl-Lys-Thr-Thr-Orn-Ser-OH×2AcOH,
   Stearinoyl-Lys-Thr-Thr-Orn-Ser-OH×2AcOH,
   Palmitoleinoyl-Lys-Thr-Thr-Orn-Ser-OH×2AcOH,
   Oleoyl-Lys-Thr-Thr-Orn-Ser-OH×2AcOH,
   Eicosaenoyl-Lys-Thr-Thr-Orn-Ser-OH×2AcOH,
   Palm-Lys-Thr-Thr-Orn-Thr-OH×2AcOH,
   Palm-Lys-Thr-Thr-Orn-Ser-OH×2AcOH,
   Palm-Lys-Thr-Thr-Orn-N-Me-Ser-OH×2AcOH,
   Palm-Lys-Thr-Thr-N-Me-Orn-Ser-OH×2AcOH,
   Palm-Lys-Thr-N-Me-Thr-Orn-Ser-OH×2AcOH,
   Palm-Lys-N-Me-Thr-Thr-Orn-Ser-OH×2AcOH,
   Palm-N-Me-Lys-Thr-Thr-Orn-Ser-OH×2AcOH,
   Palm-Lys-N-Et-Thr-Thr-Orn-Ser-OH×2AcOH,
   Palm-Lys-N-Pr-Thr-Thr-Orn-Ser-OH×2AcOH,
   $C_8H_{15}$—$SO_2$-Lys-Thr-Thr-Orn-Ser-OH×2AcOH,
   $C_{16}H_{33}$—$SO_2$-Lys-Thr-Thr-Orn-Ser-OH×2AcOH,
   $C_8F_{15}$—C(O)-Lys-Thr-Thr-Orn-Ser-OH×2AcOH, and
   H-Lys-Thr-Thr-Orn-Ser-ORetinyl×3AcOH.

4. A method for increasing the production of collagen and fibronectin in human skin by the administration of a composition according to claim 1.

5. A dermopharmaceutically and/or cosmetically active composition comprising at least one acetate salt according to claim 1, present in a quantity ranging from 0.5 ppm to 5,000 ppm (w/w), calculated on the weight of the compound of the present invention and of the bulk material(s).

6. A composition according to claim 5, wherein the composition is in a form selected from the group consisting of a solution, a dispersion, an emulsion and encapsulated in carriers, said carriers selected from the group consisting of macrocapsules, microcapsules or nanocapsules, liposomes, chylomicrons, enclosed in macro-, micro- or nanoparticles or in microfungi, and adsorbed on powdered organic and/or inorganic polymers.

7. A composition according to claim 5, wherein the composition is in a form selected from the group consisting of an emulsion, a milk, a lotion, an ointment, a gelatinous and viscous, lifting and emulsifying polymer, a pomade, a shampoo, a soap, a gel, a powder, a stick, a spray, a body oil, a face mask and a plaster for transdermal application.

8. A composition according to claim 5, wherein the composition contains commonly used ingredients selected among the group consisting of: extraction lipids and/or synthesis lipids, gelatinous and viscous, lifting and emulsifying polymers, water- or fat-soluble active agents, plant extracts, tissue extracts, marine extracts, sun protection agents, antioxidants, moisturizers and barrier agents and/or skin-revitalizing agents.

9. A composition according to claim 5, wherein the composition is a dermopharmaceutically and/or cosmetically active agent that increases the production of collagen and fibronectin in human skin.

10. A method for increasing the production of collagen and fibronectin in human skin by the administration of a composition according to claim 2.

11. A dermopharmaceutically and/or cosmetically active composition comprising at least one acetate salt according to claim 2, present in a quantity ranging from 0.5 ppm to 5,000 ppm (w/w), calculated on the weight of the compound of the present invention and of the bulk material(s).

12. A composition according to claim 11, wherein the composition is in a form selected from the group consisting of a solution, a dispersion, an emulsion and encapsulated in carriers, said carriers selected from the group consisting of macrocapsules, microcapsules or nanocapsules, liposomes or chylomicrons, enclosed in macro-, micro- or nanoparticles or in microfungi, and adsorbed on powdered organic and/or inorganic polymers.

13. A composition according to claim 11, wherein the composition is in a form selected from the group consisting of an emulsion, a milk, a lotion, an ointment, a gelatinous and viscous, lifting and emulsifying polymer, a pomade, a shampoo, a soap, a gel, a powder, a stick, a spray, a body oil, a face mask and a plaster for transdermal application.

14. A composition according to claim 11, wherein the composition contains commonly used ingredients selected among the group consisting of: extraction lipids and/or synthesis lipids, gelatinous and viscous, lifting and emulsifying polymers, water- or fat-soluble active agents, plant extracts, tissue extracts, marine extracts, sun protection agents, antioxidants, moisturizers and barrier agents and/or skin-revitalizing agents.

15. A composition according to claim 11, wherein the composition is a dermopharmaceutically and/or cosmetically active agent that increases the production of collagen and fibronectin in human skin.

16. A method for increasing the production of collagen and fibronectin in human skin by the administration of a composition according to claim 3.

17. A dermopharmaceutically and/or cosmetically active composition comprising at least one acetate salt according to claim 3, present in a quantity ranging from 0.5 ppm to 5,000 ppm (w/w), calculated on the weight of the compound of the present invention and of the bulk material(s).

18. A composition according to claim 17, wherein the composition is in a form selected from the group consisting of a solution, a dispersion, an emulsion or encapsulated in carriers said carriers selected from the group consisting of macrocapsules, microcapsules or nanocapsules, liposomes or chylomicrons, enclosed in macro-, micro- or nanoparticles or in microfungi, and adsorbed on powdered organic and/or inorganic polymers, talc or bentonite.

19. A composition according to claim 17, wherein the composition is in the form of an emulsion, a milk, a lotion, an ointment, a gelatinous and viscous, lifting and emulsifying polymer, a pomade, a shampoo, a soap, a gel, a powder, a stick, a spray, a body oil, a face mask or a plaster for transdermal application.

20. A composition according to claim 17, wherein the composition contains commonly used ingredients selected among the group consisting of: extraction lipids and/or synthesis lipids, gelatinous and viscous, lifting and emulsifying polymers, water- or fat-soluble active agents, plant extracts, tissue extracts, marine extracts, sun protection agents, antioxidants, moisturizers and barrier agents and/or skin-revitalizing agents.

21. A composition according to claim 17, wherein the composition is a dermopharmaceutically and/or cosmetically active agent that increases the production of collagen and fibronectin in human skin.

* * * * *